United States Patent [19]

Honig

[11] 4,101,446

[45] Jul. 18, 1978

[54] LEAD ACETATE IMPREGNATED MAGNESIUM SILICATE FOR THE PRODUCTION OF PERCHLOROMETHYL MERCAPTAN

[75] Inventor: Milton L. Honig, Bronx, N.Y.

[73] Assignee: Stauffer Chemical Company, Westport, Conn.

[21] Appl. No.: 753,120

[22] Filed: Dec. 22, 1976

[51] Int. Cl.$^2$ .................. B01J 21/14; B01J 31/04; C07C 145/00

[52] U.S. Cl. .................. 252/430; 252/428; 252/431 C; 260/543 H

[58] Field of Search .................. 252/431 C, 428, 430, 252/454, 457

[56] References Cited

U.S. PATENT DOCUMENTS

| | | | |
|---|---|---|---|
| 3,607,728 | 9/1971 | Wilhelm | 252/472 |
| 3,878,243 | 4/1975 | Zupancic | 260/543 H |

Primary Examiner—P. E. Konopka
Attorney, Agent, or Firm—Roger S. Benjamin

[57] ABSTRACT

A catalyst composition suitable for the production of perchloromethyl mercaptan comprising lead acetate, solvent impregnated, on magnesium silicate.

6 Claims, No Drawings

LEAD ACETATE IMPREGNATED MAGNESIUM SILICATE FOR THE PRODUCTION OF PERCHLOROMETHYL MERCAPTAN

BACKGROUND OF THE INVENTION

This invention relates to a process for the production of perchloromethyl mercaptan, by means of a catalyst comprising lead acetate, solvent impregnated, on magnesium silicate.

Perchloromethyl mercaptan, $Cl_3CSCl$, also known as trichloromethanesulfenyl chloride has commercial importance as an intermediate in the manufacture of fungicides, bactericides, germicides, herbicides, soil fumigants and pharmaceuticals.

The production of perchloromethyl mercaptan was first described by Rathke, Ann. Vol. 167, at page 195 (1873). The catalyst used for this method was essentially iodine added in the quantity of 0.1 to 1% by weight. Below about 40° C., the reaction occurs in accordance with the following equations:

(1) $CS_2 + 3Cl_2 \rightarrow CCl_3SCl + SCl_2$ (2) $2CS_2 + 5Cl_2 \rightarrow 2CCl_3SCl + S_2Cl_2$ (3) $CS_2 + 3Cl_2 \rightarrow CCl_4 + S_2Cl_2$ One of the disadvantages of the Rathke method is that in the chlorination substantial amounts of undesired byproducts, such as sulfur chlorides, thiophosgene, tetrachloromethane and the like are formed. This in turn causes a material lowering of the yield and also of the quality of the perchloromethyl mercaptan produced. The readily volatile byproducts such as carbon tetrachloride and sulfur dichloride can be separated from the reaction mixture by distillation, however, it is extremely difficult to separate the perchloromethyl mercaptan and sulfur monochloride. This is due to the fact that the respective boiling points of perchloromethyl mercaptan and sulfur monochloride differ only slightly from each other.

An additional disadvantage of the iodine catalyst is that it is soluble in the carbon disulfide reactant, and therefore must be continuously replenished.

The prior art has proposed several methods for improving the basic Rathke method. For example, U.S. Pat. No. 3,544,625 to Masat, discloses a method for producing perchloromethyl mercaptan by chlorinating carbon disulfide in the presence of a solution of inorganic acids, such as hydrochloric acid. U.S. Pat. No. 3,673,246 to Meyer et al, discloses a process for producing perchloromethyl mercaptan wherein carbon disulfide is reacted with chlorine on activated carbon at temperatures of about −5° C. to +100° C. U.S. Pat. No. 3,808,270 to Rupp et al., discloses a process for producing perchloromethyl mercaptan by reacting carbon disulfide and chlorine in a reaction zone filled with granular active carbon completely immersed in the liquid reaction mixture while maintaining temperatures in the range of about 40° to about 135° C. U.S. Pat. No. 3,878,243 to Zupancic discloses a homogeneous catalyst system comprising a lead salt of a carboxylic acid which is soluble in carbon disulfide.

The present invention has developed an improved catalyst system for the production of perchloromethyl mercaptan. Since this new catalyst system is a heterogeneous one, it is not consumed and can be used in a continuous process. Moreover, the undesirable side reaction of equation (3), which produces sulfur monochloride and carbon tetrachloride is diminished.

DESCRIPTION OF THE PREFERRED EMBODIMENT

In accordance with the present invention, an improved catalyst system for the production of perchloromethyl mercaptan has been developed. This catalyst system comprises lead acetate absorbed on hard, granular magnesium silicate, or magnesium-silica gel, commonly known as Florisil TM, a product sold by Floridin Co. It has been found that this solid catalyst system can be used continuously, whereas an iodine catalyzed system requires a batch route. In addition, improved yields and selectivity have been obtained with the lead acetate-magnesium silicate catalyst system. The term "selectivity" refers to the extent of undesirable byproducts formed, namely, $CCl_4$ and $S_2Cl_2$. A larger perchloromethyl mercaptan percentage selectivity indicates a cleaner reaction with less byproducts. As discussed previously, sulfur monochloride ($S_2Cl_2$) is particularly undesirable because of the difficulty in separating it from perchloromethyl mercaptan.

The efficacy of the lead acetate-magnesium silicate catalyst system for the production of perchloromethyl mercaptan was unexpectedly synergistic in view of the fact that both magnesium silicate and lead acetate when used alone as catalyst candidates, demonstrated substantial inactivity. Even an intimate dry 5:1 mixture of magnesium silicate to lead acetate resulted in only a 19% yield of perchloromethyl mercaptan.

It has been found that best results are obtained with a catalyst system that has been prepared by mixing an aqueous solution of finely divided lead acetate with magnesium silicate, followed by removal of water.

The preferred ratio of magnesium silicate to lead acetate is about 3:1, respectively. However, the invention can be operative for ratios up to about 10:1 and minimum ratios of about 1:3, respectively. A useful Florisil mesh size is from 60 to 100, using the U.S. or ASTM Standard Sieve Numbers. Mesh sizes from 10 thru 300 can also be effective.

The catalyst is made by dissolving lead acetate in a solvent in amounts sufficient to solubilize it. The solvents recommended for this purpose are the lower monofunctional and polyfunctional alcohols, containing from about 1 to about 4 carbon atoms, such as methanol, ethanol, glycerol and ethylene glycol. Water is a particularly preferred solvent.

Florisil is then added to the solution. The resultant mixture is stirred for about an hour. The solvent is removed in any suitable manner, such as by using an aspirator vacuum under temperature conditions varying from about 60° to about 100° C. A dry powder results which can be used as is. If desired, it can also be molded into pellets or other useful physical configurations, best suited for the reaction environment desired.

It is believed that the large surface area of magnesium silicate, combined with the activity of the impregnated lead acetate is responsible for the unexpectedly high activity of catalyst in the production of perchloromethyl mercaptan.

In the examples that follow, and throughout the specification, all parts, percentages and ratios are by weight, unless otherwise indicated.

EXAMPLE 1

A catalyst was prepared by dissolving 20 g of lead acetate trihydrate in approximately 75 ml water. The resultant solution was slowly contacted with thorough mixing with 60 g of Florisil TM (mesh size 60–100). Water was then removed by flash evaporation at 100° C. and water aspirator vacuum. A final oven drying was performed on the catalyst at 60° C/25mm over a two day period.

Twenty grams of the aforementioned catalyst were charged to a thermostated reactor containing 76 g carbon disulfide and 2 g acetylacetone (additive inhibitor). Chlorine (168 g) was then bubbled into the reactor over a five hour period. The temperature was maintained at 22° C. A total of 227 g product mixture was obtained whose composition and yields were identified by gas-liquid chromatographic (glc) analysis. Results are outlined in Table I.

EXAMPLE 2

Florisil TM (30 g) of mesh size 60–100 and lead acetate trihydrate (6 g) were intimately dry mixed. Thirty grams of this catalyst mixture along with 76 g carbon disulfide and 2 g acetylacetone were placed in a reaction vessel. The contents were thermostated at 20° C. Chlorine was bubbled into the reactor. A dry ice-acetone condenser liquefied excess chlorine allowing it to return to the reactor. After 6.5 hours only 112.8 g chlorine were absorbed. The reaction was terminated at this point, the condenser removed, and unreacted chlorine was allowed to evaporate from the vessel. Remaining behind were 135 g of product mixture. The composition of this mixture was determined by glc analysis and the results are presented in Table I.

EXAMPLE 3

Thirty grams of lead acetate deposited on Florisil TM (mesh size 60–100) were placed in a thermostated reactor. To this was further added 38 g carbon disulfide, 1 g acetylacetone and 80 g of methylene chloride as a solvent. A 20° C. temperature was maintained. Chlorine was bubbled into the solution over a 6.5 hour period. At the end of this period, 106.5 g of chlorine had been consumed. Excess gas was then vented. The product mixture weighed 182 g. Yields are reported in Table I.

EXAMPLE 4

A catalyst was prepared by mixing 20 g of lead nitrate in 80 ml. of water with 60 g of Florisil TM (mesh size 60–100). Water was subsequently removed by drying the composition in a vacuum oven.

Thirty grams of the above catalyst were charged to a reactor along with 76 g carbon disulfide and 0.38 g of an iron inhibitor. The pot temperature was kept at 25° C. throughout. Over a period of six hours, 182 g of chlorine were bubbled into the reaction mixture. Thereafter, excess gases were vented and a residue liquid weighing 281 g remained. Table I describes the composition of the product mixture.

EXAMPLE 5

A flask was charged with 76 g of carbon disulfide, 15 g of lead acetate and 2 g of acetylacetone. These reagents were stirred and thermostated at 20° C. Chlorine was bubbled into the mixture but its uptake by the reagents was poor. At the end of 6.5 hours, the solution was analyzed by glc. Only trace quantities of perchloromethyl mercaptan were found, indicating virtually no reaction. See Table I.

EXAMPLE 6

Into a flask were placed 38 g of carbon disulfide, 0.3 g of Alox TM (inhibitor equivalent to acetylacetone) and 15 g of Florisil TM (mesh size 60–100) along with 200 g of methylene chloride as solvent. These reagents were stirred and thermostated at 20° C. Chlorine was bubbled into the mixture. Uptake of chlorine was poor. At the end of 4 hours, the solution was analyzed by glc. Only trace quantities of perchloromethyl mercaptan were found, indicating virtually no reaction. See Table I.

EXAMPLE 7

A vessel was charged with 76 g of carbon disulfide, 2 g of acetylacetone and 0.5 g of iodine. The solution was stirred and the contents thermostated at 20° C. Thereupon, 182 g of chlorine was bubbled into the solution over a 5.5 hour period. The temperature was maintained at 20°–23° C. throughout. Unreacted chlorine was continuously returned to the vessel by means of a dry ice condenser. A mild vacuum was applied at the end of the reaction to remove excess chlorine. The remaining product mixture weighing 258 g was analyzed using glc. This mixture contained 71% perchloromethyl mercaptan and 34% carbon tetrachloride representing a 68% selectivety. Results are tabulated in the Table which follows:

TABLE

Summary of Perchloromethylmercaptan and Carbon Tetrachloride Yields from Catalyzed Reactions of Carbon Disulfide with Chlorine.

| EXAMPLE | CATALYST | INHIBITOR | YIELDS* % PMM | %CCl$_4$ | % PMM SELECTIVITY |
|---|---|---|---|---|---|
| 1 | Pb(OAc)$_2$ on Florisil | Acetylacetone | 76 | 21 | 78 |
| 2 | Pb(OAc)$_2$ on Florisil (physical mix) | Acetylacetone | 19 | 1 | 95 |
| 3 | Pb(OAc)$_2$ on Florisil (CH$_2$Cl$_2$ as solvent) | Acetylacetone | 37 | 7 | 84 |
| 4 | Pb(NO$_3$)$_2$ on Florisil | Dimethyl Methylphosphonate | 59 | 41 | 59 |
| 5 | Pb(OAc)$_2$ | Acetylacetone | No Reaction | | — |
| 6 | Florisil | Acetylacetone | No Reaction | | — |
| 7 | Iodine (Reference) | Acetylacetone | 71 | 34 | 68 |

*Yields based on CS$_2$ charge and are not corrected for unreacted CS$_2$. All yields based on glc analysis.

What is claimed is:

1. A catalyst composition suitable for the production of perchloromethyl mercaptan consisting essentially of lead acetate, impregnated magnesium silicate, wherein the ratio of lead acetate to magnesium silicate varies from about 3:1 to about 1:3.

2. A method for preparing a catalyst suitable for the production of perchloromethyl mercaptan which consists essentially of dissolving lead acetate in a solvent to form a solution, then contacting said solution with magnesium silicate and removing said solvent to produce a dry composition, whereby the ratio of lead acetate to magnesium silicate of said dry composition varies from about 3:1 to about 1:3.

3. A method for preparing a catalyst suitable for the production of perchloromethyl mercaptan which comprises contacting lead acetate with a solvent selected from the group consisting of methanol, ethanol, glycerol, ethylene glycol, and water, to form a solution; contacting said solution with magnesium silicate and removing said solvent to produce a dry, powdery product, whereby the ratio of lead acetate to magnesium silicate of said dry, powdery product varies from about 3:1 to about 1:3.

4. The method of claim 3 wherein the solvent is water.

5. The method of claim 3 wherein said powdery product is molded into pellets.

6. The method of claim 3 wherein said solvent is removed under vacuum conditions.

* * * * *